United States Patent
Sund et al.

(10) Patent No.: US 8,814,834 B2
(45) Date of Patent: Aug. 26, 2014

(54) INJECTOR SAFETY DEVICE

(75) Inventors: Julius Sund, Plymouth, MN (US); Eric Lagman, Anderson, SC (US); Peter Hoeft, Franconia, MN (US); Paul R. Lesch, Jr., Lino Lakes, MN (US); Tom Kramer, Coon Rapids, MN (US)

(73) Assignee: Antares Pharma, Inc., Ewing, NJ (US)

( * ) Notice: Subject to any disclaimer, the term of this patent is extended or adjusted under 35 U.S.C. 154(b) by 808 days.

(21) Appl. No.: 12/921,940

(22) PCT Filed: Mar. 10, 2009

(86) PCT No.: PCT/US2009/036682
§ 371 (c)(1),
(2), (4) Date: Jan. 19, 2011

(87) PCT Pub. No.: WO2009/114542
PCT Pub. Date: Sep. 17, 2009

(65) Prior Publication Data
US 2011/0144594 A1 Jun. 16, 2011

Related U.S. Application Data

(60) Provisional application No. 61/035,350, filed on Mar. 10, 2008.

(51) Int. Cl.
*A61M 5/315* (2006.01)
(52) U.S. Cl.
USPC .................................................... 604/220
(58) Field of Classification Search
CPC ..................... A61M 5/2033; A61M 2005/206; A61M 2005/2073; A61M 5/24; A61M 2005/208
USPC ......... 604/131, 135–137, 156, 181, 185, 187, 604/218, 220
See application file for complete search history.

(56) References Cited

U.S. PATENT DOCUMENTS 3,166,069 A * 1/1965 Enstrom et al. ................ 604/136
5,137,516 A * 8/1992 Rand et al. ..................... 604/136
(Continued)

FOREIGN PATENT DOCUMENTS

FR 2635009 2/1990
WO 94/11041 A1 5/1994
(Continued)

OTHER PUBLICATIONS

International Search Report dated Jul. 7, 2009 for International Application No. PCT/US2009/036682.
(Continued)

*Primary Examiner* — Aarti B Berdichevsky
*Assistant Examiner* — Bradley Osinski
(74) *Attorney, Agent, or Firm* — Morgan, Lewis & Bockius LLP

(57) ABSTRACT

A safety member for use with an injection device is disclosed. The safety member includes a blocking ring extending into a housing of the injection device in blocking association with a latch member associated with a trigger mechanism of the injector, in which the blocking ring blocks movement of a portion of the trigger mechanism into a firing position. The safety member further includes a manipulable portion disposed outside the housing and configured for hand-manipulation by a user to remove the safety member from the housing to unblock the firing mechanism to enable firing of the injector.

11 Claims, 12 Drawing Sheets

(56) References Cited

U.S. PATENT DOCUMENTS

| | | | |
|---|---|---|---|
| 5,665,071 A * | 9/1997 | Wyrick | 604/134 |
| 6,584,910 B1 * | 7/2003 | Plass | 102/512 |
| 2002/0188251 A1 | 12/2002 | Staylor et al. | |
| 2004/0039336 A1 * | 2/2004 | Amark et al. | 604/136 |

FOREIGN PATENT DOCUMENTS

| | | |
|---|---|---|
| WO | 00/29050 | 5/2000 |
| WO | 01/93926 A2 | 12/2001 |
| WO | 2007/047200 A1 | 4/2007 |
| WO | 2008/089886 | 7/2008 |
| WO | 2008/112472 | 9/2008 |

OTHER PUBLICATIONS

International Preliminary Report on Patentability dated Jul. 16, 2010 for International Application No. PCT/US2009/036682.

* cited by examiner

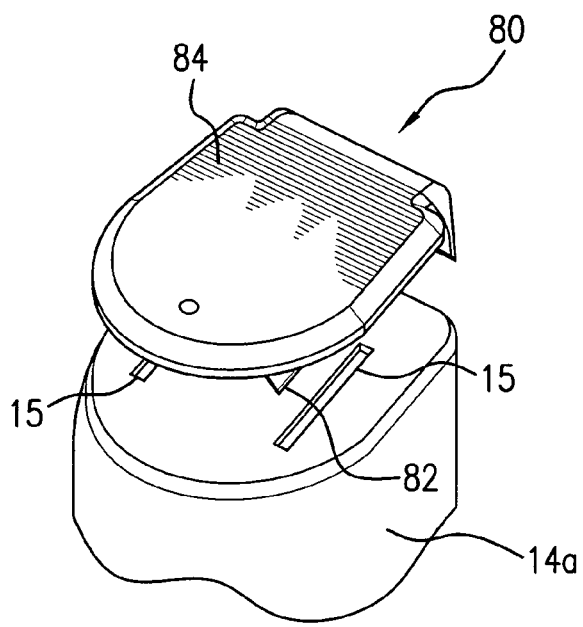 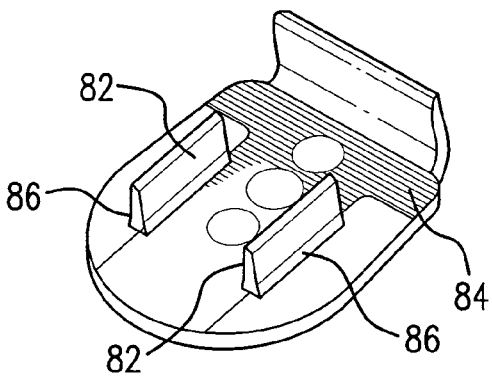
FIG.4A  FIG.4B
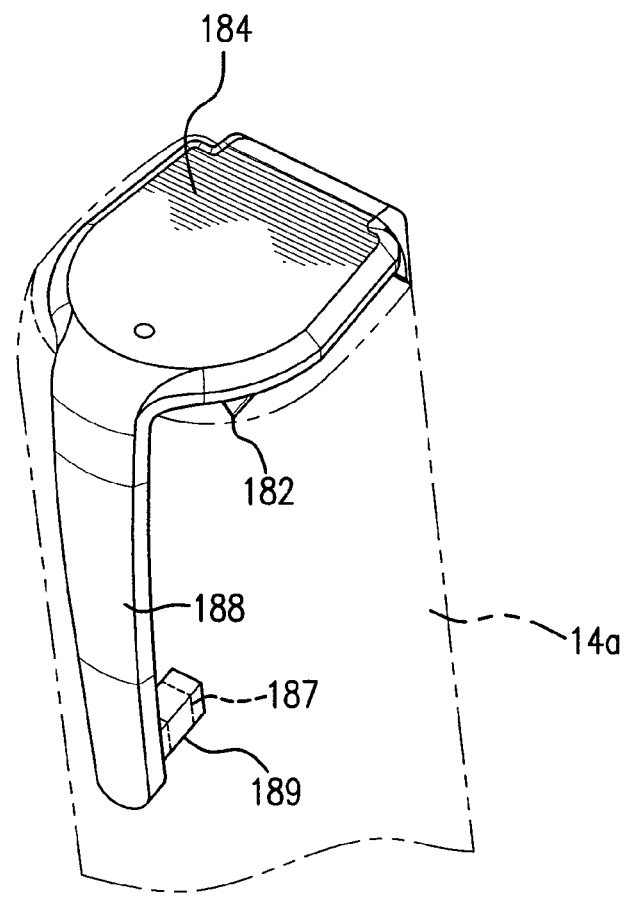
FIG.5

INJECTOR SAFETY DEVICE

FIELD OF THE INVENTION

The invention relates to injectors with safety devices, and more particularly to injectors with devices to help prevent inadvertent firing.

BACKGROUND OF THE INVENTION

Various injection devices exist that use a form of an automated mechanism to actuate injection of a liquid medicament into a patient. Examples of such devices include jet injectors, both needle-free and needle-assisted, and autoinjectors. Although the precise mechanisms used to complete injection can vary within and between these devices, most include a feature within the injection mechanism that stores kinetic energy to be used to drive the injection mechanism during use. Further, many known injection mechanisms include a trigger mechanism to secure the device such that the kinetic energy remains stored until injection is desired, whereby actuation of the trigger releases the injection mechanism, allowing the stored kinetic energy drives the injection mechanism to cause injection.

Examples of needle-free jet injectors are described in U.S. Pat. Nos. 5,599,302; 5,062,830; and 4,790,824. These traditional injectors administer medication as a fine, high velocity jet delivered under sufficient pressure to enable the jet to pass through the skin. The pressure used to deliver the medication is typically greater than approximately 4000 p.s.i. inside the compartment that contains the medicament in the injector. The injection mechanism in such needle-free jet injectors can be arranged to apply a force to a medicament storing chamber within the device such that the required pressure is created within the chamber.

Self-injectors or autoinjectors like the ones disclosed in U.S. Pat. Nos. 4,553,962 and 4,378,015 and PCT Publications WO 95/29720 and WO 97/14455 are constructed to inject medicament at a rate and in a manner similar to hand-operated hypodermic syringes. The self-injectors or autoinjectors have needles that are extended at the time of activation to penetrate the user's skin to deliver medicament through movement of the drug container and related needle. Thus the mechanism that provides the force to deliver the medicament in self-injectors and autoinjectors is also used to extend the needle and the drug container to cause the insertion of the needle through the user's skin and then to apply a force to a plunger movably disposed within the drug container to cause the medicament to be expelled from the container through the needle. The autoinjectors manufactured, for example by Owen Mumford, thus use very low pressures to inject the medicament, which is injected through a needle in a relatively slow stream. The pressures applied in the medicament-containing compartments of this type of device are very low, reaching a maximum of around 60 p.s.i. and take around 5 to 10 seconds to inject 1 mL.

Additionally, needle-assisted jet injectors have been developed that utilize a needle to initially penetrate the skin, most often to a depth less than that of a traditional hypodermic injector or autoinjectors. Once the skin is penetrated with the needle, the jet mechanism is activated, causing the medicament containing liquid within the injector to be pressurized and expelled through the needle and into the skin. The injection mechanism in needle-assisted jet injectors can be configured to move the drug container and the needle to move forward to penetrate the skin and then exert the necessary injection force to a plunger moveably disposed within the container. Alternatively, the needle and drug container can be properly positioned to penetrate the skin by bringing said needle and container to close proximity with the skin resulting in needle insertion while keeping the needle and drug container in a stationary position and the injection mechanism can be structured to pressurize the container. The pressure of the medicament within the injector can be less than that of a traditional jet injector, because the tough outer layers of the skin have already been penetrated by the needle. Similarly, the pressure of the medicament is preferably higher than that of an auto injector or the like, causing the medicament to penetrate the skin or the tissue below the skin to a depth that is sufficient so that with the needle penetration and penetration the medicament remains substantially within the body. An additional benefit of the higher pressure exists in a faster time of injection resulting in less psychological trauma to the patient and decreasing the likelihood of the user inadvertently terminating the injection prematurely by removing the injector from the injection site.

Because of the stored kinetic energy associated with the trigger and injection mechanisms, accidental firing can occur due to sudden movements during shipping or due to mishandling of the device by a user including accidental actuation of the trigger mechanism. Accidental firing of the injection mechanism can cause the medicament to be expelled from the device, which can be at a dangerously high pressure, depending on the type of injection device. Further, accidental firing can cause an injection needle to move forward with respect to the device with sufficient force to penetrate the skin.

An injector is needed that provides a reduced risk of accidental firing during shipping or handling thereof.

Additionally, many such injection devices are intended to be used a single time only. Accordingly, a locking mechanism is desired that prevents unintended repeated use thereof.

SUMMARY OF THE INVENTION

The present invention relates to an injector. The injector includes a housing and a container portion disposed within the housing. The container defines a fluid chamber containing a medicament and includes a plunger moveably disposed therein that defines a portion of the fluid chamber. The injector also includes a firing mechanism including a ram affixed to the plunger and extending axially therefrom and a latch moveably disposed within the housing and configured to engage a portion of the ram. The injector further includes a trigger moveably disposed within the housing between a ready position wherein the latch is held in engagement with the portion of the ram and a firing position wherein the latch is released, permitting movement of the ram. A safety member is positionable relative to the housing so as to restrict movement of the trigger into the firing position.

In one embodiment the housing can include an opening formed therein, and the safety member can include a blocking member having an end disposed within the housing so as to abut a portion of the trigger. In such an embodiment the blocking member extends through the opening of the housing and attaches to a body portion of the safety member that is disposed outside of the housing.

In another embodiment, the injector can further include a guard extending distally of the housing that is retractable with respect to the housing from a protecting position to an actuating position. Retraction to the actuating position can causes a portion of the guard to move the trigger into the firing position. In such an embodiment, the safety member can restrict movement of the trigger mechanism into the firing position by preventing movement of the guard into the actuating position. The safety member can include a blocking member and a body portion, the blocking member having an end disposed within the housing so as abut a portion of the guard. The blocking member can extend through an opening in the housing and into connection with the body portion, which is preferably disposed outside of the housing. Additionally or alternatively, the injector can include a sleeve affixed within the housing and configured for retaining the container, and the safety member can include a locking element slidably associated with the sleeve so as to be moveable from a first position into a second position. In such an embodiment, the first position is such that the guard is retractable into the actuating position, and the second position is such that the locking element is positioned in a fixed relationship to the sleeve and blocks movement of the guard into the actuating position. As a further addition or alternative safety member can be in the form of a cap configured to cover an open end or the guard and to surround the guard. The guard can include a flange and the cap can include a projection such that a snap-fit is achieved between the guard and the cap with a portion of the cap abutting a portion of the housing such that the cap restricts retraction of the guard into the actuating position.

BRIEF DESCRIPTION OF THE DRAWINGS

These and other objects, features and advantages of the invention will be apparent from a consideration of the following non-limiting detailed description considered in conjunction with the drawing figures, in which:

FIGS. 4A and 4B are perspective views of a safety member used in connection with the injection device of FIG. 1;

FIG. 5 is a perspective view of an alternative safety member;

DETAILED DESCRIPTION OF THE PREFERRED EMBODIMENTS

Figure 1:
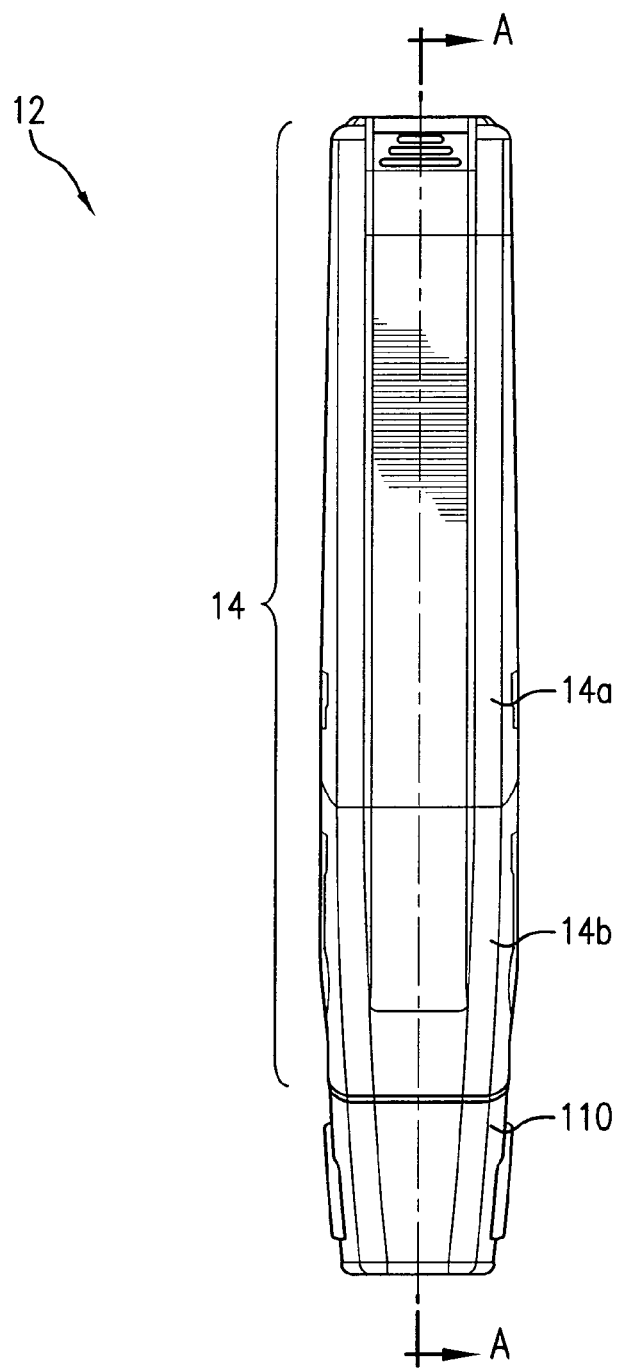
FIG. 1 is a side view of an injection device according to an embodiment of the present invention.
Figures 2, 3:
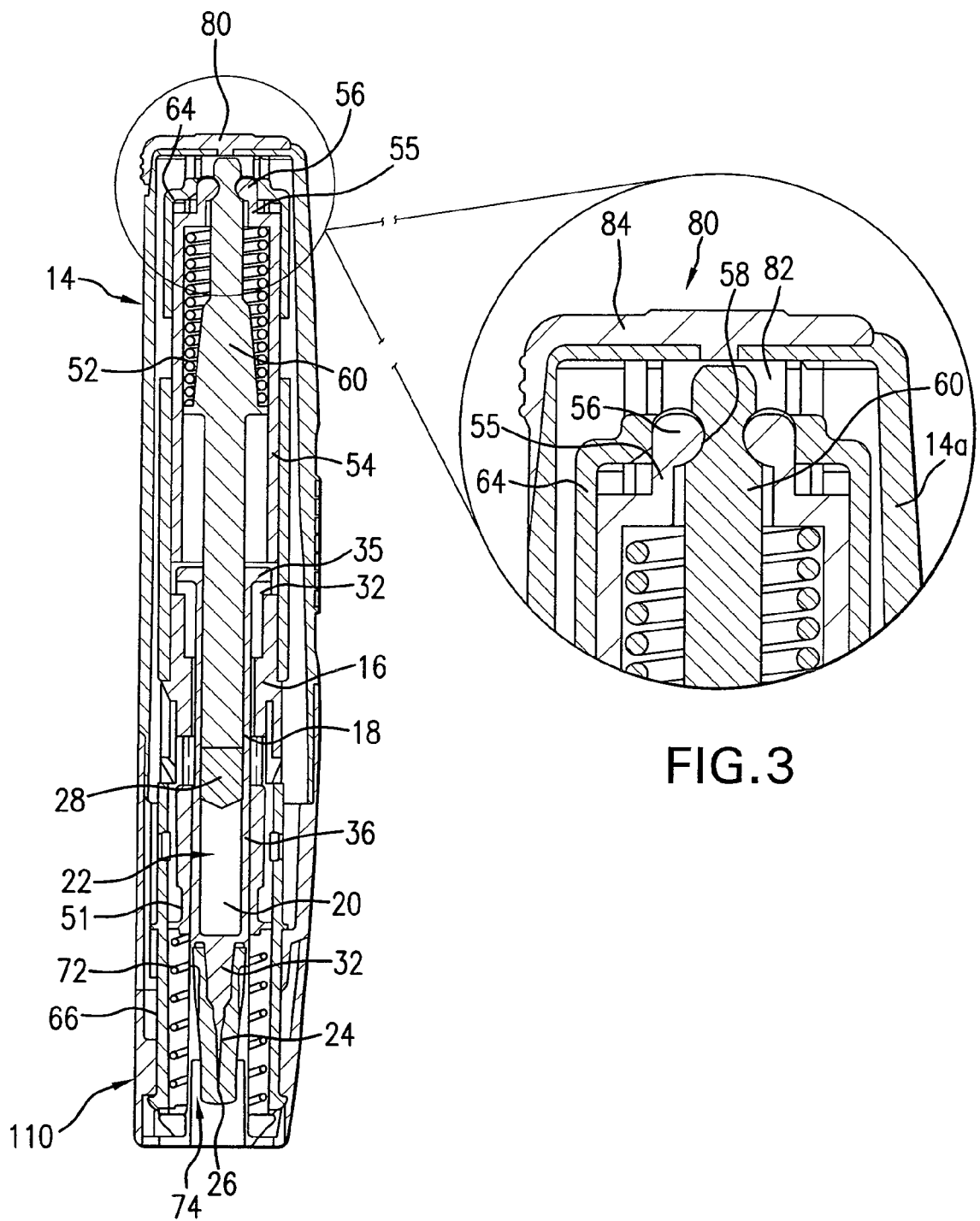
FIG. 2 is a cross-sectional view of the injection device of FIG. 1 in a safety state taken along line A-A.
FIG. 3 is an enlarged view of a portion of the cross-section shown in FIG. 2.

Referring to FIGS. 1 and 2, a preferred embodiment of an injector 12 has an outer housing 14 configured for allowing a user to handle the injector 12. Outer housing 14 substantially contains most of the components shown in FIG. 2. In an embodiment, outer housing 14 is formed from two mating portions 14a, 14b that can be configured to attach to one another by a snap or press fit or using adhesives, welding or the like shown in FIG. 1. Housing 14 includes a fluid chamber 22 therein that is configured for storing and dispensing a liquid medicament. In the embodiment shown in FIGS. 1 and 2, fluid chamber 22 is formed in a prefilled syringe 18 that fits within housing 14, but other types of fluid chambers can be used, including known types of medicament cartridges that can be prefilled, refillable, or the like. Additionally, fluid chamber 22 can be integrally formed within housing 14. A safety member 80 is located on the proximal end of outer housing 14a and is removably affixed thereto by a plurality of tabs that extend through matching openings formed in outer housing 14a to form a press-fit between safety member 80 and outer housing 14a. It is noted that, in the context of this disclosure, the terms "proximal" and "distal" are used in reference to the position of the device relative to a user of the device when held for injection of a liquid medicament into a patient. Accordingly, a point located proximal to a second point would be closer to the user and vice versa. As discussed below, safety member 80 is configured to prevent or reduce the likelihood of unintended firing of the injection device during, for example, shipping or handling of injector 12. Safety member 80 can be removed by a user of injector to allow for substantially unrestricted use of injector 12.

In a preferred embodiment sleeve 16 is housed within and mounted with the housing 12 and acts as a syringe support member. The sleeve 16 is configured to hold and position a prefilled syringe 18 of the type known in the art, such as the prefilled syringe commercially available under the name BD Hypak™ from Becton, Dickinson and Company. In the preferred embodiment, sleeve 16 is substantially fixed to the housing 14, such as by snaps, an adhesive, a weld, or another known attachment. The prefilled syringe 18 has a container portion 20 that defines in its interior a fluid chamber 22, which is prefilled with medicament to be injected. At the distal end of the prefilled syringe 18 is an injection-assisting needle 24. Needle 24 has an injecting tip 26 configured as known in the art to penetrate the tissue of a patient, preferably the skin. A needle bore extends through the needle 24, as known of the art. The bore is in fluid communication with the medicament in the fluid chamber 22 and is open at the needle tip 26 to inject the medicament. The needle bore in the needle 24 affixed to the prefilled syringe 18 is the only fluid communicating means at the distal end of the fluid chamber 22.

At a proximal side of the fluid chamber 22, opposite from the needle 24, is a plunger 28 that seals the medicament in the fluid chamber 22. A syringe wall 30 preferably comprises a tubular portion, preferably containing the needle 24 at a distal end and open at a proximal end, to define the fluid chamber 22. Plunger 28 is slideably received in the tubular portion. The prefilled syringe 20 is configured such that when the plunger 28 is displaced in a distal direction, the volume of the fluid chamber 22 is decreased, forcing the medicament out therefrom and through the bore of needle 24.

At the distal end of the fluid chamber 22 is a needle hub portion 32 to which the needle is mounted. A syringe flange 35 extends radially, preferably from the proximal end of the syringe wall 30.

In the preferred embodiment, the syringe 18 has a syringe body 36 that includes the flange 35 wall 30 and hub portion 32 is of unitary construction. A preferred material for the syringe body 36 is glass, but other materials can be used in other embodiments. A suitable prefilled syringe is the BD Hypak™, which is available in various sizes and volumes and can be prefilled with medicament. The glass of the syringe body is adhered to the needle with help of adhesives. Typical medicaments and medicament categories include epinephrine, atropine, sumatriptan, antibiotics, antidepressants, biologicals and anticoagulants. Using a prefilled syringe facilitates handling of the medicament when the injector is assembled, and there exists an extensive body of knowledge surrounding injectable dosage forms in the prefilled syringe as a small volume parenteral container.

To radially position the distal end of the prefilled syringe 18, sleeve 16 preferably has a narrowed bore portion 51 that is preferably configured to abut the outside of the syringe wall 30. The sleeve 16 can be lined with a resilient material, such as an elastomer, or it can be made unitarily with the rest of sleeve 16, such as by a series of radially-aligned, resiliently-flexible fingers 53. The elastomer can be so configured to abut the syringe 18 flange 34 at the proximal end of the sleeve 16.

A firing mechanism is preferably also contained within housing 12 and consists of a trigger 64 and a pair of resiliently deformable latches 55. The firing mechanism also includes an inner housing 54 that can be attached to the outer housing 14, such as by snaps, an adhesive, a weld, or other known attachment. Latches 55 extend from the proximal end of the inner housing 54 and can be resiliently biased outwardly. Latch protrusions 56 extend inwardly from the free ends of latches 55 and are received in a respective one of recess 58 formed in ram 60 in a blocking association therewith to prevent distal movement of the ram 60 prior to the firing of the device. The ram 60 is urged toward the distal end of the injector 12 by an energy source, which preferably is a compression spring 52, although other suitable energy sources can alternatively be used such as elastomer or compressed-gas springs, or a gas generator. A preferred type of compression spring is a coil spring.

Trigger 64 is provided exterior to the inner housing to retain the latches 55 in an inward position, thereby maintaining protrusions 56 in the blocking association in the recesses 58 to hold ram 60 in the proximal position until firing is actuated. The trigger 64 is slideable inside outer housing 14 with respect to the latches 55, preferably in an axial direction, and trigger 64 preferably surrounds the latch 54. In a preferred embodiment trigger 64 is free to move relative to outer housing 14 and relative to outer housing and is only secured in place, after the removal of safety member 80, by the pressure exerted thereon by latches 55 and friction created thereby. Preferably, nothing is present that biases trigger 64 away from the proximal end of outer housing 14, including springs or the like.

Figure 7D:
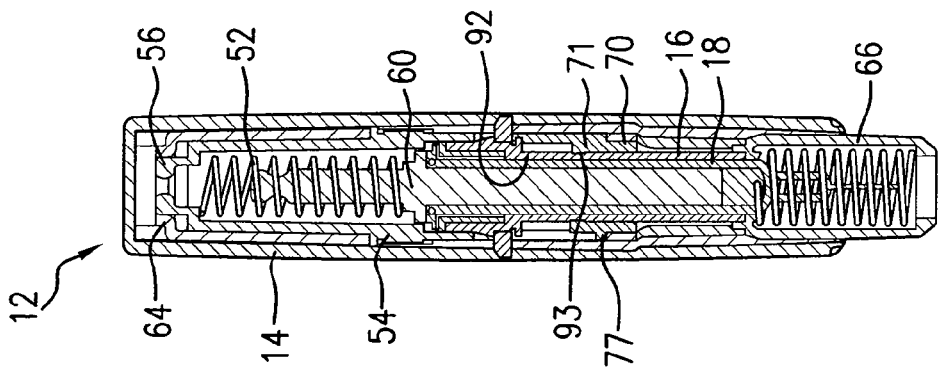
FIG. 7D is a cross-sectional view of the injection device of FIG. 1 at a locked state.
Figure 7C:
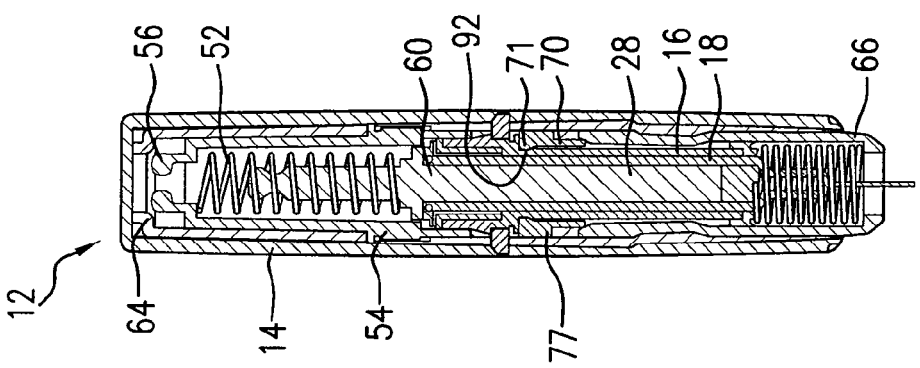
FIG. 7C is a cross-sectional view of the injection device of FIG. 1 at the end of an injection state.
Figure 7B:
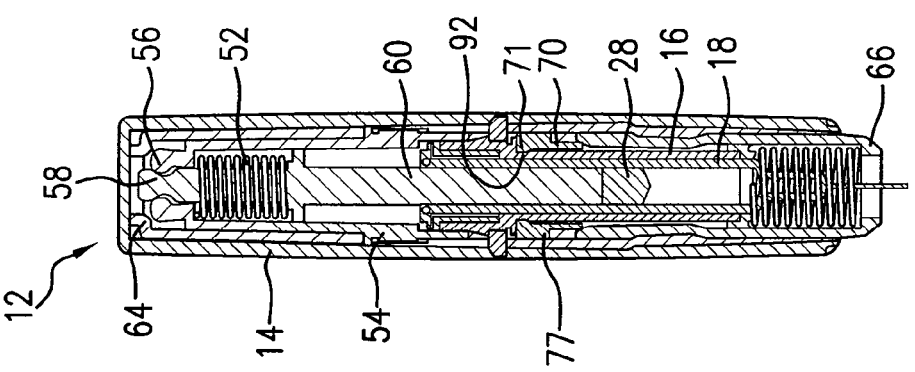
FIG. 7B is a cross-sectional view of the injection device of FIG. 1 at the start of an injection state.
Figure 7A:
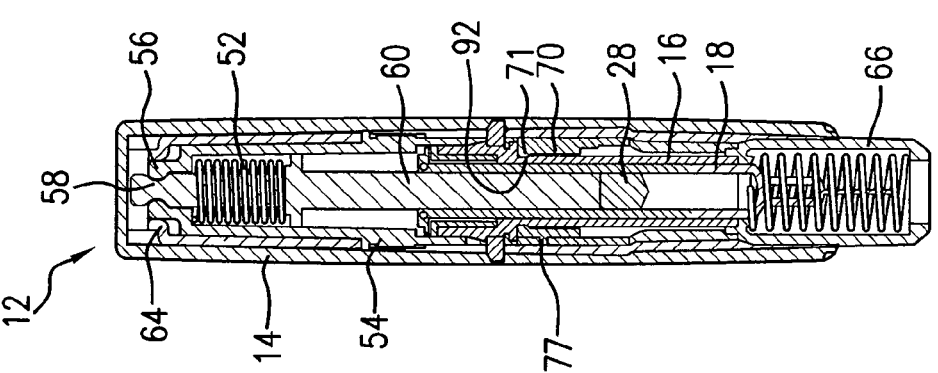
FIG. 7A is a cross-sectional view of the injection device of FIG. 1 in a ready state.
Figure 13:
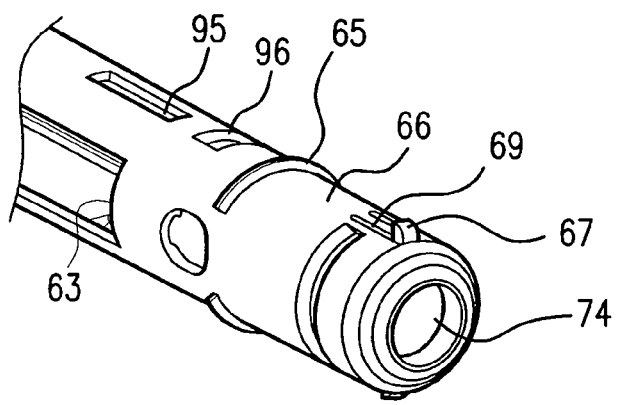
FIG. 13 is a perspective view of a needle guard according to an embodiment of the injector of FIG. 1.

The injector 12 has a needle guard 66 that is moveable with respect to the outer housing 14. The needle guard 66 is shown in FIGS. 2 and 7A in a protecting position, in which the needle 24 is disposed within the guard 66. Ridge 65 shown in FIG. 13 abuts an interior surface of outer housing 14 so as to maintain needle guard 66 within housing 14 when needle guard is fully extended into the protecting position. The needle guard 66 is retractable, preferably into the outer housing 14, in a proximal direction to an injecting position, in which the needle tip 26 and an end portion of the needle 24 are exposed as shown in FIGS. 7B and 7C for insertion into a patient. In the preferred embodiment, the proximal movement of the guard is prevented substantially at the injecting position.

Figure 6:
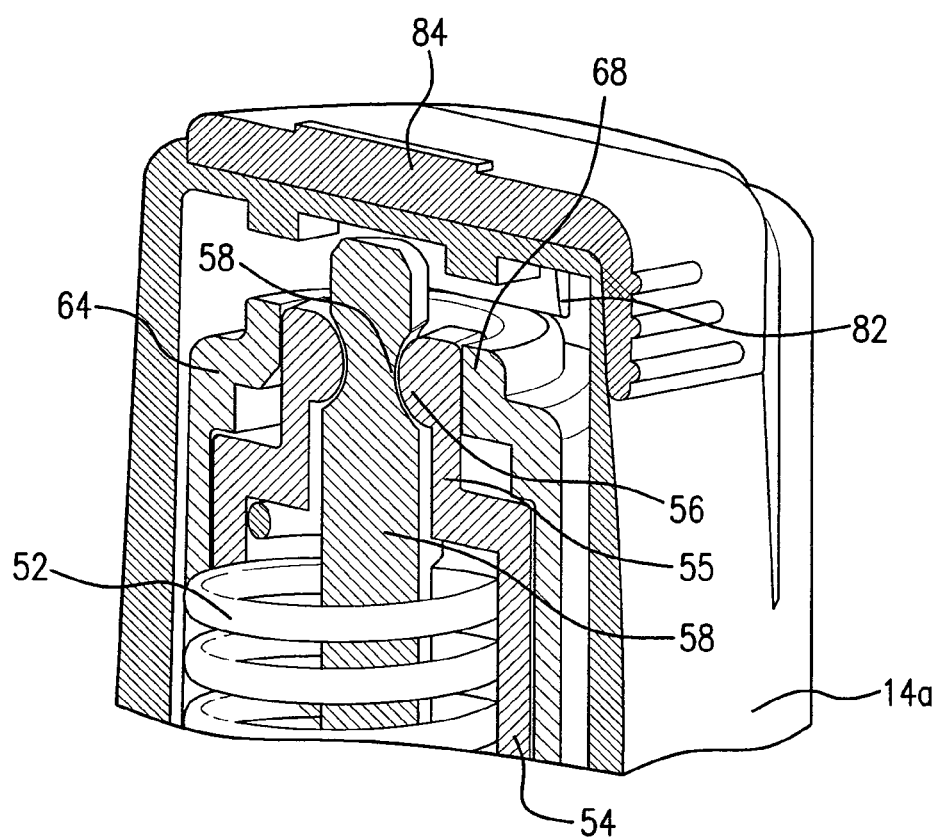
FIG. 6 is an additional cross-sectional view of the device of FIG. 1 in the safety state.

The needle guard 66 is associated with the trigger 64 such that when the guard 66 is displaced proximally it slides the trigger 64 also in a proximal direction to release protrusions 56 from the recesses 58. Preferably, the trigger 64 has a latching portion 68 (FIG. 6) that abuts the latches 55 in an association to bias and maintain the protrusions 56 positioned in the blocking association with the ram 60 prior to the firing of the device 12. When the trigger is slid proximately by the retracting of the guard 66 to the injecting position, the latching portion 68 slides beyond the portion of latches 55 that it contacts to flex the latches 55 inward to maintain protrusions 56 into the recesses 58 of the ram 60, allowing the protrusions 56 to move radially outwardly from the recess 58 and therefore from the blocking association. When this happens, spring 62 biases the ram 60 against plunger 28 to fire the jet injector.

Figure 14:
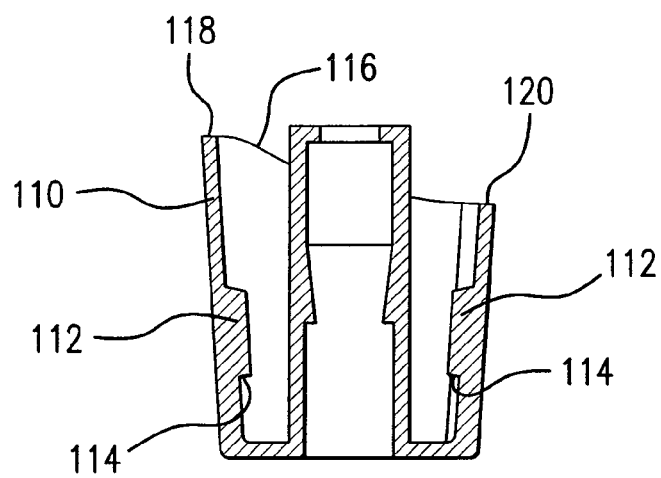
FIG. 14 is a cross-sectional view of the cap shown in FIG. 1.

Cap 110 is preferably affixable on the distal end of the device 12 so as to cover needle guard 66 and prevent accidental displacement thereof during shipping or during handling prior to preparation for injection. Cap 110 can affix to the distal end of outer housing 14 by press-fit, screw fit or the like. In a preferred embodiment, cap 110 includes a pair of projections 112 extending inwardly, as shown in FIG. 14, that form a distally-facing ridge 114. In such an embodiment, needle guard 66 is preferably formed with a pair of radially-extending flanges 67 that are configured to abut the distal ridge 114 of projection 112 to secure cap 110 to device 12. The upper edge 116 of cap 110 preferably abuts the distal end of outer housing 14 such that distal surfaces 14 of projections 12 are held against flanges 67. This arrangement of the cap 110 prevents compression of the needle guard 66 proximally into the housing, as the cap 110 is juxtaposed between the guard 66 and housing, securing needle guard 66 in the protecting position to help prevent accidental firing of the injection mechanism.

Cap 110 can be removed from device 12 by twisting cap 110 relative to housing 14 such that projections 112 are moved out of alignment with tabs 67, which allows the cap 110 to be moved distally away from needle guard 66. To prevent accidental removal of cap 110 from device 12 due to inadvertent twisting of cap 110, the cap preferably engages the housing and/or the guard to require an initially elevated force, such as requiring the cap to snap away from its closed position before completing the rotation to remove the cap. For example, upper edge 116 of cap 110 is preferably inclined, as shown in FIG. 14. The incline can include a curve, as shown, but generally the edge 116 should have one edge 118 that is higher than the other edge 120. The distal end of outer housing 14 preferably has a profile that matches that of upper edge 16 of cap 110. This arrangement requires deflection of cap 110 to allow for twisting thereof and increases the force necessary to cause cap 110 to twist relative to needle guard 66. In an alternative embodiment, the cap has a threaded or cammed association with the tabs 67, or can have another arrangement therewith so that the cap is removed by rotating.

Cap 110 is preferably attached to device 12 during assembly thereof. This can be done by properly aligning cap 110 and twisting it relative to needle guard 66 while applying a proximally-directed force thereto such that projections 112 move behind flanges 67. Alternatively, flanges 67 can be structured to be deflectable inwardly by disposing them on a corresponding tab 69 formed on needle guard 66. In such an embodiment, cap 110 can be assembled onto needle guard 66 prior to assembly of spring 72 thereinto, as spring 72 can interfere with the inward deflection of tabs 96. Alternatively, cap 110 can be resiliently deformable to allow cap 110 to be pressed onto needle guard 66 such that projections 112 pass over flanges 67.

The guard 66 is preferably resiliently biased distally towards the protecting position by compression coil spring 72. Also, the needle guard 66 has an axial opening 74 to allow the needle 24 pass there through, and which may be sized according to the type of injector desired. The construction of the present embodiment allows a user to push the distal end of the injector 12 against the patient's skin, pushing the needle 24 into the skin at an insertion location, substantially at the same speed as the injector is pushed. Once the needle 24 is fully inserted to an insertion point at a penetration depth, the trigger mechanism fires the jet injection to an injection site.

In the preferred embodiment, such as for subcutaneous injection using a needle-assisted jet injector, the guard 66 is configured to allow insertion of the needle to a penetration depth in the skin that is up to about 5 mm below the skin surface. More preferably, the penetration depth is less than about 4 mm, and in one embodiment is less than about 3 mm. Preferably, the insertion depth is at least about 0.5 mm and more preferably at least about 1 mm. In another embodiment, the distance 76 by which the needle extends past the guard 66 or the distal surface of the guard 66 that contacts the skin is up to about 5 mm, more preferably up to about 4 mm, and in one embodiment up to about 3 mm. Preferably, extension distance 76 is at least about 0.5 min, more preferably at least about 1 mm, and most preferably at least about 2 mm. In a preferred embodiment, tip 26 extends by a distance 76 of around 2.5 mm beyond the portion of the guard 66 that contacts the skin in the injecting position.

In another embodiment, such as for intramuscular injection using a needle-assisted jet injector, the injector is configured to allow the needle to be inserted into the patient to a penetration depth in the skin, or alternatively beyond the distal surface of the guard, by a distance of up to about 15 mm. In one embodiment, this distance is about between 10 mm and 14 mm. Other exposed needle lengths can be selected for jet injection to different depths below the skin, with a preferred overall penetration length of between about 0.5 mm and about 20 mm. In these embodiments, the needle guard is preferably configured for retracting from a protecting position, preferably covering the entire needle, to an injecting position, in which the desired length of the end of the needle is exposed.

As mentioned previously, safety member 80 is removably affixed to the distal end of outer housing 14. Safety member 80 includes a body portion 84 and a pair of resiliently-flexible legs 82 extending therefrom. In the embodiment shown, legs 82 are configured to extend into corresponding holes or slots 15 (FIG. 4A) formed in the proximal surface of outer housing. Legs 82 are shaped to provide a pressure fit within slots 15 to retain safety member 80 on housing 14. Legs 82 are preferably biased outwardly and can further include tabs 86 disposed out the outside surfaces thereof to engage the inside of outer housing 14 at the location of slots 15 to further the retention of safety member 80 onto outer housing 14. Legs 82 are further preferably shaped to allow a user to remove safety member from outer housing 14, when injection is desired. Legs 82 should, however, prevent safety member 80 from becoming accidentally or unintentionally dislodged from its attachment to outer housing 14.

Legs 82 are further configured to abut the proximal-most surface of the trigger 64, preferably the latching portion 68. The abutment of legs 82 against latching portion 68 preferably hinders or prevents jostling or other motion of trigger 64 in the proximal direction, which would cause the injection mechanism to fire. In an embodiment, it is possible to cause safety member 80 to become dislodged from outer housing 14 by forced proximal movement of guard 66, causing latching portion 64 to push proximally on legs 82 such that they are pushed out of the slots in which they are received. Legs 82, however, are preferably configured in relationship to housing 14 and the firing mechanism such that the force necessary for latching portion 68 to force legs 82 out of slots 15 is sufficient to prevent trigger 64 from being jostled out of position due to vibration during shipping or from acute shock during shipping or handling caused by dropping of device 12. Further preferably, safety member is preferably configured to require a force of between 1 and 10 lbs applied, for example, by the user of the device for removal thereof from the outer housing 14. In a preferred embodiment, between about 2.5 and about 5 lbs of force is required for removal of safety member 80 from outer housing 14.

An alternative embodiment of safety member 180 is shown in FIG. 5. In this embodiment, body portion 184 forms an elongated tab 188 that extends along the outside of outer housing 14. The end of tab 188 includes a projection 189 that is configured to fit within a corresponding opening 187 formed within outer housing 14. In this embodiment, the interaction between projection 189 and the corresponding opening 187 further secures safety member 180 to outer housing, further preventing safety member 180 from becoming unintentionally dislodged from housing 114b. Safety member 180 is preferably configured such that elongated tab 188 is of an appropriate length to extend through its properly-positioned corresponding opening 187 and into the interior of outer housing 114 to a position that is proximal of guard 66, and distal of trigger 64. Such an arrangement blocks movement of guard 66 such that it is prevented from moving proximally and into contact with trigger 64 upon an unintentional or accidental force being applied to guard 64.

Figure 8:
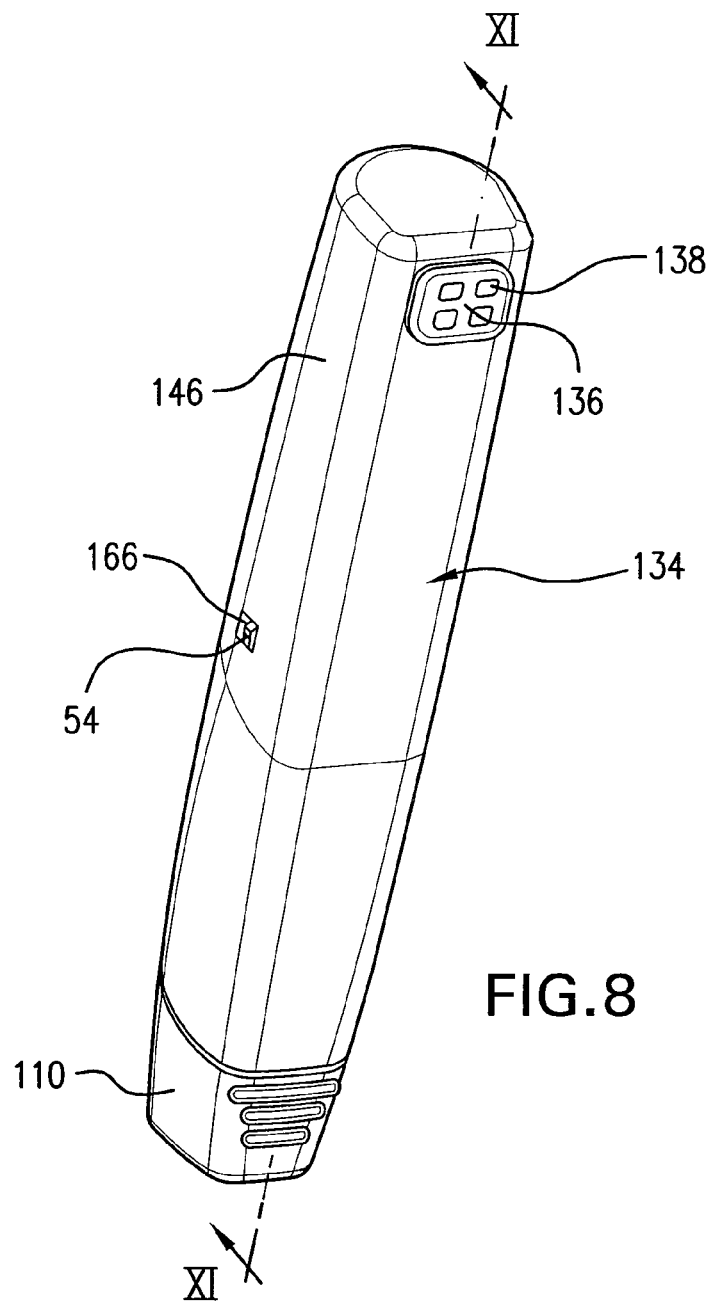
FIG. 8 is a perspective view of an injection device according to a further alternative embodiment of the present invention.
Figure 9:
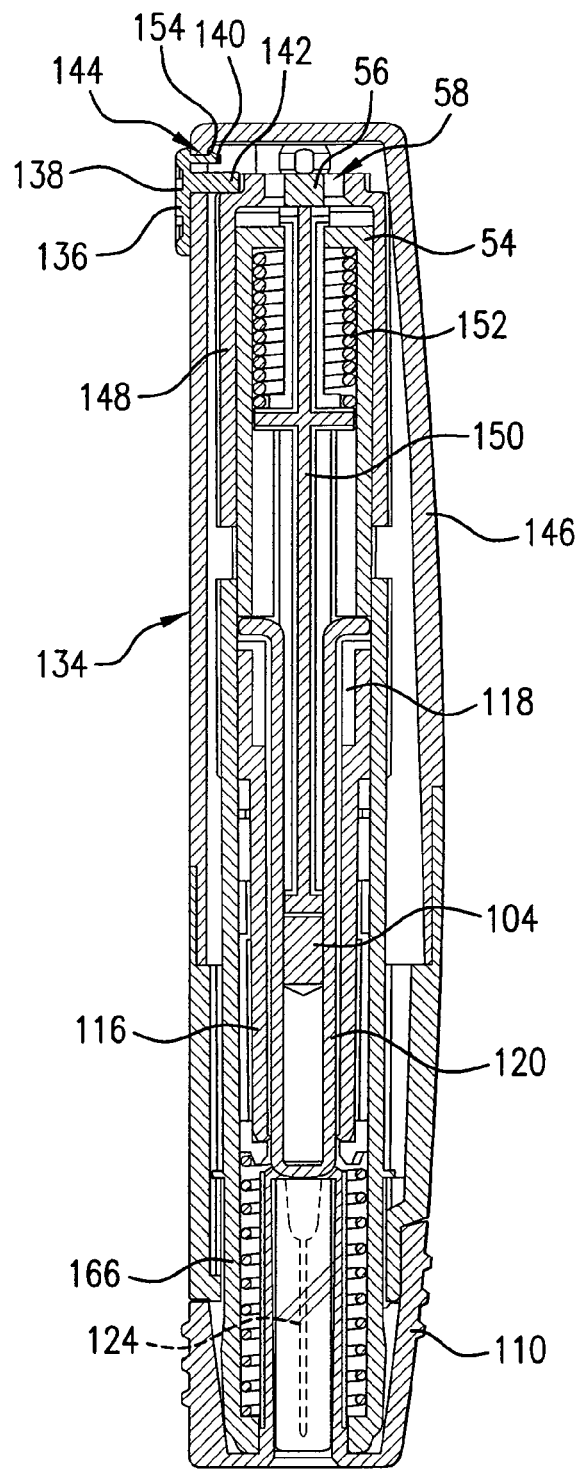
FIG. 9 is a cross-sectional view of the injection device of FIG. 8.

In an alternative embodiment of injector 134, shown in FIGS. 8 and 9, a safety member 136 is included that has an outer, manipulable handling-portion 138, a catch member 140, and a blocking ring 142. The catch and blocking rings 140,142 are received in a safety opening 144 in the proximal portion of the housing 146, preferably extending radially from the handling portion 138, which is disposed outside the injector housing 146.

In the arrangement shown, the safety member 136 is in a safety position, associated with the injector 134 with the blocking ring 142 in a blocking association with the trigger 148. In the safety position, the blocking ring 142 blocks accidental movement of the trigger 148 in a proximal, axial direction, which movement would cause the release of latch protrusions 56 from the recess 58 of ram 150, allowing spring 152 to bias the ram 150 to fire the injection. The trigger 148 is preferably bell-shaped, which provides additional proximal, axial surface to abut and be blocked by the blocking ring 142 in the blocking position.

In this embodiment, without the safety member 136 in the safety position, the trigger 148 could accidentally slide proximally, such as due to a shock or vibration, and cause the injector to fire unintentionally. Also, without the safety member 136 in the safety position, accidental depression of the guard 66 would move the trigger 148 proximally, causing the injector 134 to fire.

The catch member 140 preferably has an enlarged or curved tip 154 to provide a snap fit with the injector housing 146 to retain the safety member 136 in the engaged in the safety position with the injector housing 146 and prevent or inhibit accidental dislodging of the safety member 136 from the safety opening 144. The preferred catch member 140 is resiliently flexible, and sufficiently pliant to enable removal of the safety member 136 from the injector housing 146 by grasping and pulling the handling portion 138 with a user's finger tips, before intentionally firing the injector 134.

Figure 10:
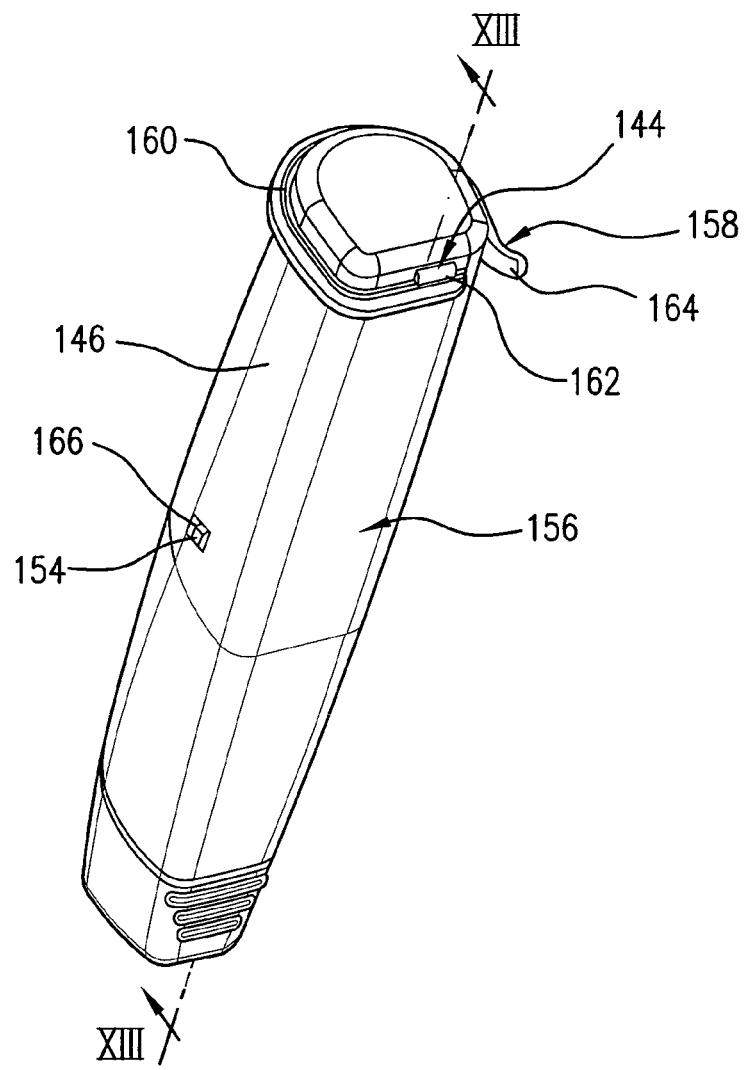
FIG. 10 is a perspective view of an injection device according to a further alternative embodiment of the present invention.
Figure 11:
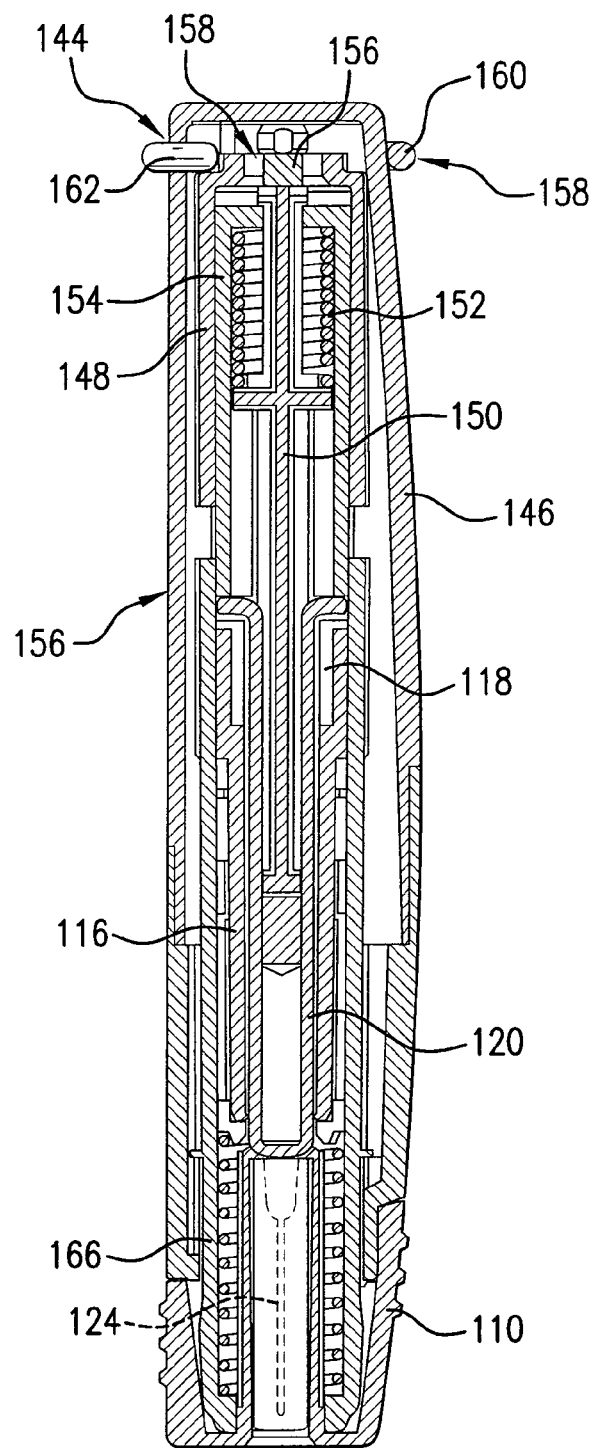
FIG. 11 is a cross-sectional view of the injection device of FIG. 10.

Referring to FIGS. 10 and 11, injector 156 includes a safety member 158 with a flexible body 160, which is preferably resiliently flexible and extends circumferentially around the exterior of the injector housing 146. The safety member 158 has a free tail 164 that is preferably angled away from the housing 146 in the safety position shown, to facilitate pushing the tail 164 up over the proximal side of the injector 156 with a user's fingers to disengage and remove the safety member 158 from the injector housing 146.

A blocking ring 162 of the safety member 158 is received in safety opening 144. In the safety position, blocking ring 162 is in a blocking association with trigger 148 to block movement of the trigger 148 in a proximal, axial direction to prevent inadvertent firing of the injector, as described above.

The safety members described herein can be used with other types of injectors, including needle-assisted jet-injectors that do not employ prefilled syringes, with needle-free injectors, and with other types of powered injectors. Jet injectors especially benefit from this safety mechanism due to the power of their injection when fired, even when fired inadvertently. The safety members 80,136,158 are preferably made of a unitary piece, such as of a resilient plastic or metal, although other suitable constructions and materials can be used.

In the preferred embodiment of a needle-assisted jet injector, the spring 62 and the prefilled syringe 18 are configured to jet inject the medicament. Thus, the spring 62 applies a force on the plunger 28 that is sufficient to elevate the pressure within the fluid chamber 22 to a level high enough to eject the medicament from the needle 24 as a jet. Jet injection is to be understood as an injection with sufficient velocity and force to disperse the medicament to locations remote from the needle tip 26 and thus minimize leakback at the injection site.

Figure 15:
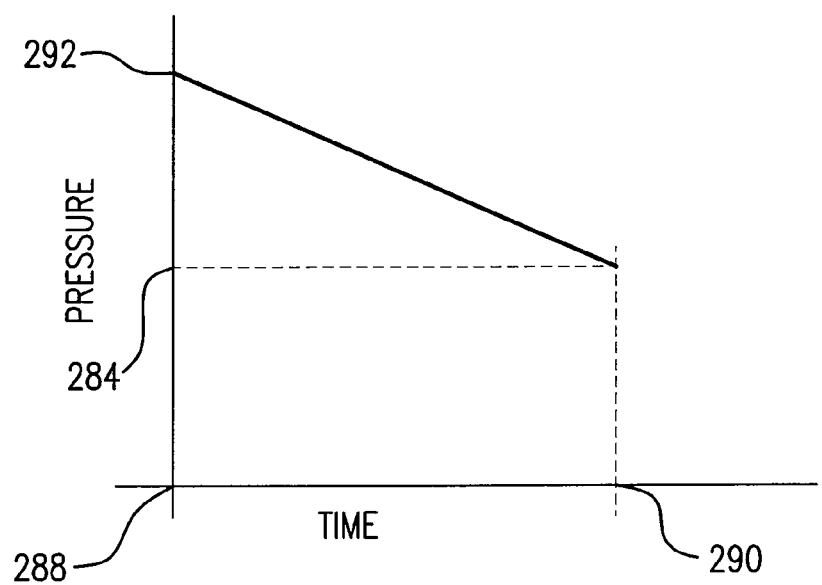
FIG. 15 is a graph showing the pressure within the liquid chamber of a preferred injection device as a function of time.

The graph shown in FIG. 15 shows a pressure-profile over time for a firing mechanism associated with an exemplary type of injector with witch the presently-disclosed safety devices can be used. While the pressure profile shown is of the type typically associated with jet injection, a person of ordinary skill in the art would understand that the various embodiments of the invention disclosed herein are not limited, however, to jet injection, but would also be useful, for example, with other types of injection utilizing stored kinetic energy. Referring to the graph shown in FIG. 15, numeral 288 represents the point in time when a preferred embodiment of device 12 is fired, and numeral 290 represents the point of completion of the medicament injection, preferably when the plunger 28 hits the forward wall of the container portion 220. Numeral 292 represents the initial and peak pressure during the injection, and numeral 294 represents the final and low pressure during the injection. Because the spring 62 of the preferred embodiment has a linear spring constant and an injection-assisting needle is used to puncture the skin before commencing the injection, the pressure drops substantially linearly from the start of the injection 288 until the injection is completed. The final pressure 294 at the end 290 of the injection is sufficiently elevated so that even at the end of the firing stroke of ram 60, the medicament is still jet injected, and a very small amount or none of the medicament is deposited in a bolus around the needle tip 26.

Preferably the peak pressure during the injection, using the preferred needle-assisted jet injector, is less than about 1,000 p.s.i., more preferably less than 500 p.s.i., and most preferably less than about 350 p.s.i. At the end 80 of the injection, the pressure 84 applied to the medicament in the fluid chamber 22 is preferably at least about 80 p.s.i., more preferably at least about 90 p.s.i., and most preferably at least about 100 p.s.i. In one embodiment of the invention, the initial pressure 82 is around 330 p.s.i., and the final pressure is about 180 p.s.i., while in another embodiment the initial pressure 292 is about 300 p.s.i., dropping to around 110 p.s.i. at the end 284 of the injection. Other injection rates are used for other embodiments discussed herein. For example, needle-free jet injectors can use an injection pressure in the range of about 4,000 p.s.i. or greater. Furthermore, autoinjectors can use an injection pressure in the range of about 60 p.s.i. or less. The needles used in the preferred embodiment is between 26 and 28 gauge, and are most preferably around 27 gauge, but alternatively other needle gages can be used where the other components are cooperatively configured to produce the desired injection. Preferably, the components of the injector 12 are configured to jet inject the medicament to a subterraneous injection site.

The amount of medicament contained and injected from fluid chamber 22 is preferably between about 0.02 mL and 4 mL, and preferably less than about 3 mL, and in the preferred embodiment is around 1 mL. Larger volumes may also be selected depending on the particular medicament and dosage required. Preferably, the prefilled syringe is assembled into the remaining parts of the jet injector 12 already containing the desired amount of medicament. In a preferred embodiment, the prefilled syringe contains about 1 mL of medicament.

Preferred injection rates are below about 1.0 mL/sec., more preferably below about 0.8 mL/sec., and preferably at least about 0.4 mL/sec., more preferably at least about 0.5 mL/sec, and most preferably between about 0.60 and about 0.75 mL/sec. Preferably, the injection of the entire amount of medicament is completed in less than about 2 seconds, more preferably in less than about 1.5 seconds, and most preferably in less than about 1 seconds. Preferably, the medicament injection takes at least about 0.5 second, and more preferably at least 0.6 seconds. A preferred embodiment injects the medicament at about 0.67 mL/sec., completing the injection of 0.5 mL in about 0.75 seconds. Other injection rates however, are possible for the alternative embodiments of device 12 discussed herein.

U.S. Pat. No. 6,391,003 discloses several experimental results of pressures that can be applied to medicament in a glass cartridge, using 26 and 27 gage needles. The following table illustrates exemplary injections with different peak pressures that can be used with glass prefilled syringes:

| Pressure and Time (sec.) to Inject 1 cc | | |
|---|---|---|
| Pressure | 26 Gauge needle | 27 Gauge needle |
| 150 p.s.i. | 2.1 | 4.2 |
| 200 p.s.i. | 1.9 | 3.9 |
| 240 p.s.i. | 1.7 | 3.3 |
| 375 p.s.i. | 1.4 | 3.1 |

It is foreseen that higher pressures and flow rates will be used with shorter needle penetration into the patient skin to achieve jet injections to a particular desired depth substantially without medicament leakback. Alternative embodiments can use higher or lower injection pressures. For instance, needle-free injectors will typically use higher pressures to penetrate the skin without a needle, and autoinjectors will use lower pressures to simulate a hand-powered syringe injection.

It has been found that using the needle-assisted jet injection of the preferred embodiment, short needles can be used to inject medicament to different parts of the skin, preferably subcutaneously, substantially without any leakback. Using a needle that extends by about 2.5 mm from the needle guard 66, a 27 gauge needle 24, and a pressure in the fluid chamber 22 peaking at around 300 p.s.i. and ending at around 100 p.s.i., resulting in a flow rate of about 0.5 mL/sec., 1 mL of medicament has been found to successfully be injected without leakback in close to 100% of the tested injections. Thus, the needle-assisted jet injector of the present invention permits jet injection of the medicament using a very short needle reliably regardless of the thickness of the patient's skin or the patient's age, weight or other factors.

In a preferred embodiment, device 12 includes a locking element, such as a locking ring 70 associated with the injection mechanism. As shown in FIGS. 7A-7D, locking ring 70 is preferably disposed between sleeve 16 and needle guard 66, and interacts with sleeve 16 and needle guard 66 such that locking ring permits needle guard 66 to move relative to outer housing 14 through a single injection cycle. This includes movement from the protecting position (FIG. 7A) into the injecting position (FIGS. 7B, 7C) and then to return to the protecting position (FIG. 7D) under the force of compression spring 72 once injection is complete. When needle guard 16 returns to the protecting position at the end of the injection cycle, locking ring is positioned relative to sleeve 16 and needle guard 66 such that further movement therebetween is restricted.

Figure 12:
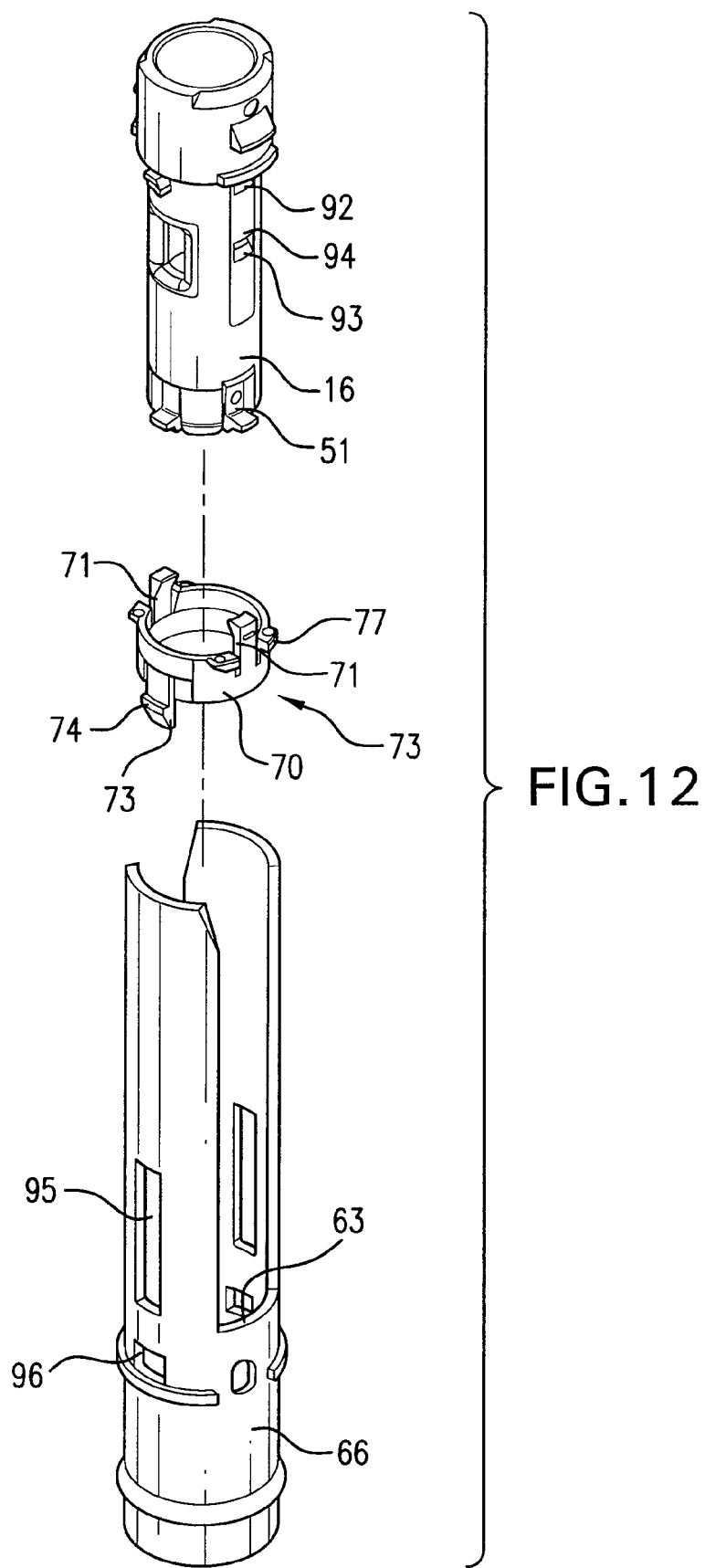
FIG. 12 is an exploded view of a portion of the trigger mechanism associated with the injection device of FIG. 1.

As shown in FIGS. 7A-7D, movement of needle guard 66 through one locking cycle causes locking ring 70 to move relative to sleeve 16 from an injecting position to a locking position. In the injecting position locking ring 70 is disposed such that the upper arms 71 of locking ring 70 engage a portion of the device that is associated with the medicament chamber, such as proximal notches 92 formed in the outer surface of sleeve 16. The engagement of upper arms 71 within proximal notches 92 releasably maintains locking ring 70 in the injecting position. As shown in FIG. 12, locking ring 70 can be generally annular in shape so as to surround the medicament chamber, either directly or indirectly such as by surrounding sleeve 16. Locking ring 70 further includes a pair of lower arms 73, each having a tab 74 formed on the end thereof. When locking ring is in the injecting position, tabs 74 are received in slot 95 formed in needle guard 66 such that needle guard is slideable through a predetermined distance over locking ring 70. As needle guard 66 is moved into the injecting position with respect to outer housing 14, needle guard 66 slides over locking ring 70 such that tabs 74 reach the end of slot 95 and are depressed inwardly, allowing needle guard 66 to continue to move into the injecting position. When the injecting position is reached, tabs 74 align with holes 96 of needle guard 66, allowing lower arms 73 to return to their natural position, wherein the upper surfaces of tabs 74 engage an edge of the holes 96, thereby coupling locking ring 70 to needle guard 66.

As needle guard 66 returns to the protecting position, needle guard 66 pulls distally on locking ring 70, causing upper arms 71 to release from proximal notches 92.

Preferably, upper arms 71 and proximal notches 92 are formed with mating inclined surfaces such that the inclined surfaces of upper arms 71 engage another portion of the device that is associated with the medicament chamber, such as by extending into proximal notches 92 but are forced outwardly by distally-directed movement relative thereto. This configuration allows the needle guard 66 to cause locking ring 70 to move therewith and out of the injecting position as needle guard moves distally toward the protecting position over sleeve 16, which remains stationary.

When needle guard 66 reaches the protecting position, upper arms 71 move over distal notches 93 formed in sleeve 16 such that the upper surfaces 75 of upper arms 71 engage the upper surface 94 of distal notches 93. Further, in such a position, flange 77 of locking ring 70 abuts surface 67 of needle guard to block needle guard 66 from distal motion relative to locking ring 70. This engagement prevents locking ring from moving proximally with respect to sleeve 16. Because locking ring 72 is coupled to needle guard 66, and because sleeve 16 is attached to outer housing, needle guard 66 is locked relative to outer housing 14, and is prevented from being moved back into the injecting position. This prevents needle 24 from being accidentally exposed after use of device 12.

All of the references specifically identified in the detailed description section of the present application are expressly incorporated herein in their entirety by reference thereto. The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments may be devised by those skilled in the art. For example, the features for the various embodiments can be used in other embodiments. In an alternative embodiment, the hosing can be fixed to the bracket, and the inner portion, defining at least the bottom of the chutes can slide in and out of the housing. Therefore, it will be understood that the appended claims are intended to cover all such modifications and embodiments that come within the spirit and scope of the present invention.

What is claimed is:

1. An injector, comprising:
   a housing;
   a container portion disposed within the housing, defining a fluid chamber containing a medicament, and including a plunger moveably disposed therein and defining a portion of the fluid chamber;
   a firing mechanism including a ram affixed to the plunger and extending axially therefrom;
   a latch moveably disposed within the housing and configured to engage a portion of the ram;
   a trigger moveably disposed within the housing between a ready position wherein the latch is held in engagement with the portion of the ram and a firing position wherein the latch is released, permitting movement of the ram;
   a safety member that is positionable relative to the housing so as to restrict movement of the trigger into the firing position; and
   a guard extending distally of the housing, the guard being retractable with respect to the housing from a protecting position to an actuating position, wherein retraction to the actuating position causes a portion of the guard to move the trigger into the firing position, wherein the safety member restricts movement of the trigger mechanism into the firing position by preventing movement of the guard into the actuating position; and
   wherein the housing includes an opening formed therein, and wherein the safety member includes a blocking member having an end disposed within the housing so as to abut a portion of the trigger, the blocking member extending through the opening of the housing and attaching to a body portion of the safety member that is disposed outside of the housing.

2. The injector of claim 1, wherein the blocking member is retained within the opening in the housing by a snap fit and is configured to be removed by a user to permit movement of the trigger into the firing position.

3. The injector of claim 1, wherein the trigger is moveable from the ready position to the firing position by a force in a first amount, and wherein a frictional relationship is present between the trigger and the latch creating a retaining force between the trigger and the latch in a second amount, and wherein the safety member restricts the movement of the trigger into the firing position by providing a safety force to the trigger in a third amount such that the first amount is greater than the second amount by about 2.5 lbs.

4. The injector of claim 1, wherein the latch includes a flexible arm and a projection, wherein the ram includes an indentation, wherein the projection is receivable within the indentation, and wherein the projection is held within the indentation when the trigger abuts the latch in the ready position.

5. The injector of claim 4, wherein the indentation and the projection are configured such that the latch restricts movement of the ram when the projection is held in the indentation by the trigger and such that movement of the trigger into the firing position allows the projection and the indentation to disengage and the ram to move axially relative to the latch.

6. The injector of claim 1 further including a needle having a tip and being associated with the chamber for penetrating the skin of a patient for injection of the medicament, wherein the guard has a distal end that is positioned distally of the needle tip when the guard is in the protecting position, and wherein the distal end of the guard is positioned proximally of the needle tip when the guard is in the retracted position.

7. The injector of claim 1, wherein the housing includes an opening and wherein the safety member includes a blocking member and a body portion, the blocking member having an end disposed within the housing so as abut a portion of the guard, the blocking member extending through the opening in the housing and into connection with the body portion, and wherein the body portion is disposed outside of the housing.

8. The injector of claim 7, wherein the guard includes a proximal end and wherein the trigger includes a distal end, wherein the proximal end of the guard is disposed axially remote from the distal end of the trigger when the guard is in the guarding position, and wherein the blocking member is disposed axially between the proximal end of the guard and the distal end of the trigger.

9. The injector of claim 1, wherein the injector includes a sleeve affixed within the housing and configured for retaining the container, and wherein the safety member includes a locking element slidably associated with the sleeve so as to be moveable from a first position into a second position, wherein the first position is such that the guard is retractable into the actuating position, and wherein in the second position the locking element is positioned in a fixed relationship to the sleeve and blocks movement of the guard into the actuating position.

10. The injector of claim 9 further including a spring positioned within the housing to resiliently bias the guard toward the protecting position such that subsequent to retraction of the guard into the actuating position, the guard returns to the protecting position, wherein the retraction of the guard engages the guard with the locking member, and wherein the subsequent return of the guard to the protecting position moves the locking element into the second position.

11. The injector of claim 1, wherein the safety member is in the form of a cap configured to cover an open end or the guard and to surround the guard, wherein the guard includes a flange and the cap includes a projection such that a snap-fit is achieved between the guard and the cap, a portion of the cap abutting a portion of the housing such that the cap restricts retraction of the guard into the actuating position.

* * * * *